(12) United States Patent
Hansen et al.

(10) Patent No.: US 7,790,852 B2
(45) Date of Patent: Sep. 7, 2010

(54) LIQUID COMPOSITION OF FACTOR VII POLYPEPTIDES

(75) Inventors: Birthe Lykkegaard Hansen, Vaerloese (DK); Michael Bech Jensen, Alleroed (DK); Troels Kornfelt, Virum (DK)

(73) Assignee: Novo Nordisk Health Care A/G, Zurich (CH)

( * ) Notice: Subject to any disclaimer, the term of this patent is extended or adjusted under 35 U.S.C. 154(b) by 0 days.

(21) Appl. No.: 12/154,088

(22) Filed: May 20, 2008

(65) Prior Publication Data

US 2008/0227715 A1   Sep. 18, 2008

Related U.S. Application Data

(63) Continuation of application No. 11/304,429, filed on Dec. 15, 2005, now abandoned, which is a continuation of application No. PCT/DK2004/000447, filed on Jun. 24, 2004.

(60) Provisional application No. 60/484,334, filed on Jul. 2, 2003.

(30) Foreign Application Priority Data

Jun. 25, 2003   (DK) ............................... 2003 00959

(51) Int. Cl.
*A61K 38/48* (2006.01)
(52) U.S. Cl. .................................................... 530/384
(58) Field of Classification Search ...................... None
See application file for complete search history.

(56) References Cited

U.S. PATENT DOCUMENTS

| | | | |
|---|---|---|---|
| 0,115,590 A | 6/1871 | Flood et al. | |
| 4,297,344 A | 10/1981 | Schwinn et al. | |
| 4,404,132 A | 9/1983 | Mitra | |
| 4,495,278 A | 1/1985 | Thomas | |
| 4,784,950 A | 11/1988 | Hagen et al. | |
| 4,956,386 A | 9/1990 | McLoughlin et al. | |
| 5,180,583 A | 1/1993 | Hedner | |
| 5,576,291 A | 11/1996 | Curtis et al. | |
| 5,649,959 A | 7/1997 | Hannam et al. | |
| 5,700,914 A | 12/1997 | Jorgensen et al. | |
| 5,770,700 A | 6/1998 | Webb et al. | |
| 5,804,420 A | 9/1998 | Chan et al. | |
| 5,824,780 A | 10/1998 | Curtis et al. | |
| 5,830,852 A * | 11/1998 | Thatcher et al. ................. 514/3 |
| 5,831,026 A | 11/1998 | Almstedt et al. | |
| 5,925,738 A | 7/1999 | Miekka et al. | |
| 5,927,739 A | 7/1999 | Spira et al. | |
| 5,962,650 A | 10/1999 | Osterberg et al. | |
| 5,993,795 A | 11/1999 | Osawa et al. | |
| 6,034,222 A | 3/2000 | Fischer et al. | |
| 6,228,620 B1 | 5/2001 | Chapman et al. | |
| 6,277,828 B1 | 8/2001 | Knepp et al. | |
| 6,310,183 B1 * | 10/2001 | Johannessen et al. ........ 530/384 |
| 6,320,029 B1 | 11/2001 | Miekka et al. | |
| 6,586,573 B1 | 7/2003 | Besman et al. | |
| 6,586,574 B1 | 7/2003 | Hansen | |
| 6,599,724 B1 | 7/2003 | Mikaelsson et al. | |
| 6,825,323 B2 | 11/2004 | Hess | |
| 6,833,352 B2 | 12/2004 | Johannessen et al. | |
| 6,903,069 B2 * | 6/2005 | Pingel et al. ..................... 514/2 |
| 2001/0031721 A1 | 10/2001 | Webb | |
| 2002/0110552 A1 | 8/2002 | Romisch et al. | |
| 2002/0115590 A1 | 8/2002 | Johannessen et al. | |
| 2004/0009918 A1 * | 1/2004 | Nedergaard et al. ........... 514/12 |
| 2004/0043933 A1 | 3/2004 | Hansen et al. | |
| 2007/0049523 A1 | 3/2007 | Hansen et al. | |
| 2009/0075895 A1 | 3/2009 | Nedergaard | |
| 2010/0136622 A1 | 6/2010 | Krarup | |

FOREIGN PATENT DOCUMENTS

| | | |
|---|---|---|
| AU | 2003/289742 | 7/2007 |
| CA | 2304396 | 4/1999 |
| EP | 0052874 | 6/1982 |
| EP | 225160 | 6/1987 |
| EP | 547932 | 6/1993 |
| EP | 765669 | 8/1995 |
| EP | 770625 | 10/1995 |
| EP | 0872487 | 10/1998 |
| EP | 1232753 | 9/1999 |
| JP | 62-195335 | 8/1987 |
| JP | 3155797 | 7/1991 |
| JP | 6-504678 | 6/1994 |

(Continued)

OTHER PUBLICATIONS

Cleland et al., Crit Rev in Thera Drug Carr Sys, vol. 10(4), pp. 307-377 (1993).

(Continued)

*Primary Examiner*—Suzanne M. Noakes
(74) *Attorney, Agent, or Firm*—Shelby J. Walker

(57) ABSTRACT

The invention concerns a liquid aqueous composition comprising (i) a factor VII polypeptide, (ii) an agent suitable for keeping pH in the range of from about 4.0 to about 9.0; (iii) an agent selected from the group consisting of: a calcium salt, a magnesium salt, or a mixture thereof; wherein the concentration of (iii) is less than 15 mM; and (iv) An ionic strength modifying agent; wherein the ionic strength of the composition is at least 200 mM.

27 Claims, 1 Drawing Sheet

FOREIGN PATENT DOCUMENTS

| | | |
|---|---|---|
| JP | 8-0509745 | 10/1996 |
| JP | 11-500408 | 1/1999 |
| JP | 2000-513720 | 10/2000 |
| WO | WO 88/00210 | 1/1988 |
| WO | WO 91/10439 | 7/1991 |
| WO | WO 92/15686 | 9/1992 |
| WO | WO 93/00807 | 1/1993 |
| WO | WO 94/05692 | 3/1994 |
| WO | WO 94/22905 | 10/1994 |
| WO | WO 94/26286 | 11/1994 |
| WO | WO 94/27631 | 12/1994 |
| WO | WO 95/28954 | 11/1995 |
| WO | WO 96/12800 * | 5/1996 |
| WO | WO 97/19687 * | 6/1997 |
| WO | WO 97/26909 | 7/1997 |
| WO | WO 97/47651 | 12/1997 |
| WO | WO 98/22619 | 5/1998 |
| WO | WO 99/66031 | 12/1999 |
| WO | WO 00/20835 | 4/2000 |
| WO | WO 00/48635 | 8/2000 |
| WO | WO 2004/048635 | 8/2000 |
| WO | WO 01/03726 | 1/2001 |
| WO | WO 01/12653 | 2/2001 |
| WO | WO 01/58935 | 8/2001 |
| WO | WO 01/82943 | 11/2001 |
| WO | WO 01/85198 | 11/2001 |
| WO | WO 01/85199 | 11/2001 |
| WO | WO 02/22776 | 3/2002 |
| WO | WO 03/007868 | 1/2003 |
| WO | WO 03/055511 | 7/2003 |
| WO | WO 03/055512 | 7/2003 |
| WO | WO 03/092731 | 11/2003 |
| WO | WO 2004/000347 | 12/2003 |
| WO | WO 2004/008635 | 1/2004 |

OTHER PUBLICATIONS

Cooper, Arthur J.L., Ann Rev Biochem, vol. 52, pp. 187-222 (1983).
International Search Report for PCT/DK03/00419, Oct. 20, 2003.
International Search Report for PCT/DK2004/000181, Sep. 2, 2005.
Laegemiddel Kataloget, pp. 893-894 (2000) translation.
Manning et al., Pharm Res, vol. 6(11), pp. 903-918 (1989).
NovoSeven® Coagulation Factor VIIa (Recombinant) Package Insert, Mar. 8, 1999.
Porter, C.W. et al., Biochem & Biophysical Research Communications, vol. 122(1), pp. 350-357 (1984).
Wang, International Journal of Pharmaceutics, vol. 203, pp. 1-60 (2000).
Wang et al., J. Parenter Sci Technol, vol. 42(10), pp. 4-26 (1988).
English translation of Enziklopedia lekarstv. M., RLS-2001, 468; Encyclopedia of drugs, p. 468.
International Search Report dated Oct. 20, 2003.
Laegemiddel Kataloget, pp. 893-894 (2000) and the English translation attached to it.
Wang et al., Journal of Parenteral Science & Technology, vol. 42, Supplement, pp. S3-S26 (1988).
Wells, Biochemistry, vol. 29, pp. 8509-8517 (1990).
Bach, Ronald et al., Blood, vol. 63, Part 2, pp. 393-398 (1984).
Bajaj, S. Paul et al, Journal of Biological Chemistry, vol. 256, Part1, pp. 253-259 (1981).
Broze, Jr., George J. et al., Journal of Biological Chemistry, vol. 255, Part 4, pp. 1242-1247 (1980).
Brozovic et al., J. Clin. Path., 1971, vol. 24, pp. 690-693.
Dike et al., British Journal of Haematology, vol. 45 pp. 107-118 (1980).
Dombrose et al., Thrombosis Research, vol. 3, pp. 737-743 (1973).
English language abstract of JP11500408.
English language abstract of JP08509745.
Husi, Holger et al, Journal of Chromatography, vol. 736, pp. 77-88 (1999).
International Search Report completed Jan. 28, 2005.
International Search Report Mailed Jul. 22, 2004 for Pct/Dk2004/000183.
Jesty, Jolyon et al, Journal of Biological Chemistry, vol. 249, Part 2, pp. 509-515 (1974).
Klausen, N.K. et al., Analysis of the Glycoforms of human recombinant factor VIIa by capillary electrophoresis and high-performance liquid chromatography, Journal of Chromatography, vol. 718, pp. 195-202 (1995).
Krarup, J.C. et al., Abstract, American Chemical Society, vol. 255 (1-2), pp. BIO333 (2003).
Liebman, Howard A. et al., Proceedings of the National Academy of Sciences of the USA, vol. 82, pp. 3879-3883 (1985).
Nemerson, Yale et al, Proceedings of the National Academy of Sciences of the USA, vol. 70, Part 2, pp. 310-314 (1973).
Non-final Office Action mailed Oct. 1, 2008 in U.S. Appl. No. 11/229,428 filed on Sep. 15, 2005 by Krarup et al.
Notice of Allowance mailed Jan. 12, 2010 in U.S. Appl. No. 11/229,428 filed on Sep. 15, 2005 by Krarup et al.
Notice of Allowance mailed Aug. 28, 2009 in U.S. Appl. No. 11/229,428 filed on Sep. 15, 2005 by Krarup et al.
Notice of Allowance mailed May 28, 2009 in U.S. Appl. No. 11/229,428 filed on Sep. 15, 2005 by Krarup et al.
O'Brien, Donogh P. et al, Blood, vol. 78, Part 1, pp. 132-140 (1991).
Rao, L.V.M. et al, Analytical Biochemistry, vol. 136, Part 2, pp. 357-361 (1984).
Ruiz, Sonia M., et al, Thrombosis Research, vol. 98, pp. 203-211 (2000).
Tomokiyo, K. et al., Large-scale production and properties of human plasma-derived activated Factor VII concentrate, Vox Sanguinis, vol. 84, pp. 54-64 (2003).
Yan, S. Betty, Journal of Molecular Recognition, vol. 9 pp. 211-218 (1996).
Abandonment mailed on Nov. 9, 2009 in U.S. Appl. No. 11/229,427 filed Sep. 15, 2005 by Jensen et al.
Abandonment mailed on Apr. 17, 2007 in U.S. Appl. No. 11/304,427 filed Dec. 15, 2005 by Jensen et al.
Final Office Action mailed on Jul. 31, 2009 in U.S. Appl. No. 10/602,838 filed Jun. 24, 2003 by Hansen et al.
Final Office Action mailed on Feb. 7, 2008 in U.S. Appl. No. 10/602,838 filed Jun. 24, 2003 by Hansen et al.
Final Office Action mailed on Oct. 12, 2006 in U.S. Appl. No. 10/602,838 filed Jun. 24, 2003 by Hansen et al.
Final Office Action mailed on Jan. 27, 2009 in U.S. Appl. No. 11/229,427 filed Sep. 15, 2005 by Jensen et al.
Final Office Action mailed on May 2, 2008 in U.S. Appl. No. 11/304,427 filed Dec. 15, 2005 by Jensen et al.
Final Office Action mailed on Dec. 30, 2009 in U.S. Appl. No. 11/473,387 filed Jun. 21, 2006 by Hansen et al.
Non-final Office Action mailed on Feb. 6, 2009 in U.S. Appl. No. 10/602,838 filed Jun. 24, 2003 by Hansen et al.
Non-final Office Action mailed on May 31, 2007 in U.S. Appl. No. 10/602,838 filed Jun. 24, 2003 by Hansen et al.
Non-final Office Action mailed on Feb. 7, 2006 in U.S. App. No. 10/602,838 filed Jun. 24, 2003 by Hansen et al.
Non-final Office Action mailed on Jun. 25, 2008 in U.S. Appl. No. 11/229,427 filed Sep. 15, 2005 by Jensen et al.
Non-final Office Action mailed on Nov. 21, 2007 in U.S. Appl. No. 11/229,427 filed Sep. 15, 2005 by Jensen et al.
Non-final Office Action mailed on Feb. 6, 2009 in U.S. Appl. No. 11/304,427 filed Dec. 15, 2005 by Jensen et al.
Non-final Office Action mailed on Sep. 11, 2007 in U.S. Appl. No. 11/304,427 filed Dec. 15, 2005 by Jensen et al.
Non-final Office Action mailed on Jan. 29, 2009 in U.S. Appl. No. 11/473,387 filed Jun. 21, 2006 by Hansen et al.
Non-final Office Action mailed on Apr. 8, 2008 in U.S. Appl. No. 11/473,387 filed Jun. 21, 2006 by Hansen et al.
Non-final Office Action mailed on Jan. 4, 2010 in U.S. Appl. No. 11/526,503 filed Sep. 25, 2006 by Jensen et al.
Non-final Office Action mailed on Apr. 6, 2009 in U.S. Appl. No. 11/526,503 filed Sep. 25, 2006 by Jensen et al.
Notice of Allowance mailed on Dec. 8, 2009 in U.S. Appl. No. 10/602,838 filed Jun. 24, 2003 by Hansen et al.

Notice of Allowance mailed on Jun. 12, 2009 in U.S. Appl. No. 11/229,427 filed Sep. 15, 2005 by Jensen et al.
Notice of Allowance mailed on Dec. 6, 2009 in U.S. Appl. No. 11/304,427 filed Sep. 15, 2005 by Jensen et al.
Abandonment dated Aug. 2, 2006, issued in U.S. Appl. No. 10/602,340 (filed Jun. 23, 2003 by Hansen).
Abandonment dated Oct. 27, 2006, issued in U.S. Appl. No. 10/609,780 (filed Jun. 30, 2003 by Jensen).
Non-Final Office Action dated Jul. 2, 2010, issued U.S. Appl. No. 12/536,872 (filed Aug. 6, 2009 by Jensen).
Non-Final Office Action dated Jul. 7, 2010, issued in U.S. Appl. No. 12/407,266 (filed Mar. 19, 2009 by Hansen).
Non-Final Office Action dated Mar. 27, 2006, issued in U.S. Appl. No. 10/609,780 (filed Jun. 30, 2003 by Jensen).
Notice of Allowance dated Apr. 8, 2010, issued in U.S. Appl. No. 11/304,427 (filed Dec. 15, 2005 by. Jensen et al.).
Notice of Allowance dated Jun. 22, 2010, issued in U.S. Appl. No. 10/602,838 (filed Jun. 24, 2003 by Hansen et al.).
Notice of Allowance dated Mar. 29, 2010, issued in U.S. Appl. No. 10/602,838 (filed Jun. 24, 2003 by Hansen et al.).
Notice of Allowance dated May 6, 2010, issued U.S. Appl. No. 11/229,428 (filed Sep. 15, 2005 by Krarup).
Abandonment dated Jun. 10, 2008, issued in U.S. Appl. No. 11/304,429 (filed Dec. 15, 2005 by Hansen et al.).
Non-Final Office Action dated Nov. 20, 2007, issued in U.S. Appl. No. 11/304,429 (filed Dec. 15, 2005 by Hansen et al.).
Non-Final Office Action dated Apr. 18, 2007, issued in U.S. Appl. No. 11/304,429 (filed Dec. 15, 2005 by Hansen et al.).
Abandonment dated Jun. 10, 2008, issued in U.S. Appl. No. 11/304,429 (filed Dec. 15, 2005 by Hansen et al.).
Non-Final Office Action dated Sep. 19, 2010, issued in U.S. Appl. No. 11/450,783 (filed Jun. 9, 2003 by Hansen et al.).
Abandonment dated January 5, 2009, issued in U.S. Appl. No. 10/427,395 (filed May 1, 2003 by Nedergaard et al.).
Non-Final Office Action dated May 30, 2008, issued in U.S. Appl. No. 10/427,395 (filed May 1, 2003 by Nedergaard et al.).
Non-Final Office Action dated Jun. 14, 2006, issued in U.S. Appl. No. 10/427,395 (filed May 1, 2003 by Nedergaard et al.).
Final Office Action dated Mar. 17, 2009, issued in U.S. Appl. No. 10/427,395 (filed May 1, 2003 by Nedergaard et al.).

* cited by examiner

LIQUID COMPOSITION OF FACTOR VII POLYPEPTIDES

CROSS-REFERENCE TO RELATED APPLICATIONS

This application is a continuation of U.S. application Ser. No. 11/304,429 filed Dec. 15, 2005 which is a continuation of International application No. PCT/DK2004/000447 filed Jun. 24, 2004 and claims priority of Danish application No. PA 2003 00959 filed Jun. 25, 2003, priority of U.S. application No. 60/484,334 filed Jul. 2, 2003, and priority of international application No. PCT/DK2004/000181 filed Mar. 18, 2004.

FIELD OF THE INVENTION

The present invention is directed to liquid aqueous compositions containing factor VII polypeptides, and to methods for making and using such compositions. More particularly, this invention relates to liquid compositions stabilised against chemical and/or physical degradation.

BACKGROUND OF THE INVENTION

A variety of factors involved in the blood clotting process have been identified, including factor VII (FVII), a plasma glycoprotein. Haemostasis is initiated by the formation of a complex between tissue factor (TF) being exposed to the circulating blood following an injury to the vessel wall, and FVIIa which is present in the circulation in an amount corresponding to about 1% of the total FVII protein mass. FVII exists in plasma mainly as a single-chain zymogen, which is cleaved by FXa into its two-chain, activated form, FVIIa. Recombinant activated factor VIIa (rFVIIa) has been developed as a pro-haemostatic agent. The administration of rFVIIa offers a rapid and highly effective pro-haemostatic response in haemophilic subjects with bleedings who cannot be treated with other coagulation factor products due to antibody formation. Also bleeding in subjects with factor VII deficiency or subjects having a normal coagulation system but experiencing excessive bleeding can be treated successfully with FVIIa.

It is desirable to have administration forms of factor VIIa suitable for both storage and for delivery. Ideally, the drug product is stored and administered as a liquid. Alternatively, the drug product is lyophilized, i.e., freeze-dried, and then reconstituted by adding a suitable diluent just prior to patient use. Ideally, the drug product has sufficient stability to be kept in long-term storage, i.e., more than six months.

The decision to either maintain the finished drug product as a liquid or to freeze-dry it is usually based on the stability of the protein drug in those forms. Protein stability can be affected inter alia by such factors as ionic strength, pH, temperature, repeated cycles of freeze/thaw, and exposures to shear forces. Active protein may be lost as a result of physical instabilities, including denaturation and aggregation (both soluble and insoluble aggregate formation), as well as chemical instabilities, including, for example, hydrolysis, deamidation, and oxidation, to name just a few. For a general review of stability of protein pharmaceuticals, see, for example, Manning, et al., Pharmaceutical Research 6:903-918 (1989).

While the possible occurrence of protein instabilities is widely appreciated, it is impossible to predict particular instability problems of a particular protein. Any of these instabilities can result in the formation of a protein by-product, or derivative, having lowered activity, increased toxicity, and/or increased immunogenicity. Indeed, protein precipitation may lead to thrombosis, non-homogeneity of dosage form and amount, as well as clogged syringes.

Furthermore, post-translational modifications such as, for example, gamma carboxylation of certain glutamic acid residues in the N-terminus and addition of carbohydrate side chains provide potential sites that may be susceptible to modification upon storage. Also, specific to factor VIIa, being a serine protease, fragmentation due to autocatalysis may occur (enzymatic degradation). Thus, the safety and efficacy of any composition of a protein is directly related to its stability. Maintaining stability in a liquid form is generally different from a lyophilized form because of greatly increased potential for molecular motion and therefore increased probability of molecular interactions. Maintaining stability in a concentrated form is also different because of the propensity for aggregate formation at increased protein concentrations.

When developing a liquid composition, many factors are taken into consideration. Short-term, i.e., less than six months, liquid stability generally depends on avoiding gross structural changes, such as denaturation and aggregation. These processes are described in the literature for a number of proteins, and many examples of stabilizing agents exist. It is well known that an agent effective at stabilizing one protein actually acts to destabilize another. Once the protein has been stabilized against gross structural changes, developing a liquid composition for long-term stability (e.g., greater than six months) depends on further stabilizing the protein from types of degradation specific to that protein. More specific types of degradation may include, for example, disulfide bond scrambling, oxidation of certain residues, deamidation, cyclization. Although it is not always possible to pinpoint the individual degradation species, assays are developed to monitor subtle changes so as to monitor the ability of specific excipients to uniquely stabilize the protein of interest.

In addition to stability considerations, one generally selects excipients, which are approved by various worldwide medical regulatory agencies. It is desirable that the pH of the composition is in a physiologically suitable range upon injection/infusion, otherwise pain and discomfort for the patient may result.

For a general review of protein compositions, see, for example, Cleland et al.: The development of stable protein compositions: A closer look at protein aggregation, deamidation and oxidation, Critical Reviews in Therapeutic Drug Carrier Systems 1993, 10(4): 307-377; and Wang et al., Parenteral compositions of proteins and peptides: Stability and stabilizers, Journal of Parenteral Science and Technology 1988 (Supplement), 42 (2S).

Other publications of interest regarding stabilization of proteins are as follows.

U.S. 20010031721 A1 (American Home Products) concerns highly concentrated, lyophilised, and liquid factor IX compositions.

U.S. Pat. No. 5,770,700 (Genetics Institute) concerns liquid factor IX compositions.

WO 97/19687 (American Red Cross) concerns liquid compositions of plasma proteins, in particular factor VIII and factor IX.

U.S. Pat. No. 4,297,344 discloses stabilization of coagulation factors II and VIII, antithrombin III, and plasminogen against heat by adding selected amino acids such as glycine, alanine, hydroxyproline, glutamine, and aminobutyric acid, and a carbohydrate such as a monosaccharide, an oligosaccharide, or a sugar alcohol.

Factor VIIa undergoes several degradative pathways, especially aggregation (dimerisation), oxidation, and autolytic cleavage (clipping of the peptide backbone). Furthermore, precipitation may occur. Many of these reactions can be slowed significantly by removal of water from the protein. However, the development of an aqueous composition for factor VIIa has the advantages of eliminating reconstitution errors, thereby increasing dosing accuracy, as well as simplifying the use of the product clinically, thereby increasing patient compliance. Ideally, compositions of factor VIIa should be stable for more than 6 months over a wide range of protein concentrations. This allows for flexibility in methods of administration. Generally, more highly concentrated forms allow for the administration of lower volumes, which is highly desirable from the patients' point of view. Liquid compositions can have many advantages over freeze-dried products with regard to ease of administration and use.

Today, the only commercially available, recombinantly-made FVII polypeptide composition is a freeze-dried factor FVIIa product which is reconstituted before use; it contains a relatively low factor VIIa concentration, e.g., about 0.6 mg/ml. A vial (1.2 mg) of NovoSeven® (Novo Nordisk A/S, Denmark) contains 1.2 mg recombinant human factor VIIa, 5.84 mg NaCl, 2.94 mg CaCl2, 2H2O, 2.64 mg GlyGly, 0.14 mg polysorbate 80, and 60.0 mg mannitol; it is reconstituted to pH 5.5 by 2.0 ml water for injection (WFI). When reconstituted, the protein solution is stable for use for 24 hours. Thus, no liquid ready-for use- or concentrated factor VII products are currently commercially available.

Accordingly, there is a need in the art for methods for improving stability of factor VII polypeptides, including human factor VIIa (chemical and/or physical stability), increasing the concentration, maintaining activity levels, and providing liquid compositions suitable for storage. Thus, it is an objective of this invention to provide an aqueous factor VII polypeptide composition which provides acceptable control of chemical and/or physical degradation products such as enzymatic degradation or autocatalysis products.

SUMMARY OF THE INVENTION

The present inventors have now found that factor VII or analogues thereof (i) ("factor VII polypeptides"), when formulated in aqueous solution at an ionic strength of at least 200 mM are stable in the pH range from about 4 to about 9.

Thus, in one aspect, the present invention provides a liquid aqueous composition comprising a factor VII polypeptide (i); a buffering agent (ii) suitable for keeping pH in the range of from about 4.0 to about 9.0; an agent (iii) selected from the list of: a calcium salt, a magnesium salt, or a mixture thereof; wherein the concentration of (iii) is less than 15 mM; and an ionic strength modifying agent (iv); wherein the ionic strength of the composition is at least about 200 mM.

In a second aspect, the invention also provides a method for preparing a liquid, aqueous composition of a factor VII polypeptide, comprising the step of providing the factor VII polypeptide in a solution comprising a buffering agent (ii) suitable for keeping pH in the range of from about 4.0 to about 9.0; an agent (iii) selected from the list of: a calcium salt, a magnesium salt, or a mixture thereof, wherein the concentration of (iii) is less than 15 mM; and an ionic strength modifying agent (iv); while ensuring that, in the final composition, the ionic strength of the composition is at least about 200 mM.

In a third aspect, the invention also concerns the use of a composition as defined above for use as a medicament.

In a fourth aspect, the invention also concerns the use of a composition as defined above for the preparation of a medicament for treating a factor VII-responsive syndrome.

In a fifth aspect, the present invention relates to a method for treating a factor VII-responsive syndrome, the method comprising administering to a subject in need thereof, under conditions that result in a decrease in bleeding and/or an increase in blood clotting, an effective amount of a liquid, aqueous composition as defined above.

In a sixth aspect, the invention relates to a method for reducing degradation of Factor VII in a liquid formulation, said method comprising the step of providing the factor VII polypeptide in a solution comprising a buffering agent (ii) suitable for keeping pH in the range of from about 4.0 to about 9.0; an agent (iii) selected from the list of: a calcium salt, a magnesium salt, or a mixture thereof; wherein the concentration of (iii) is less than 15 mM; and an ionic strength modifying agent (iv); while ensuring that, in the final composition, the ionic strength is at least 200 mM.

In a seventh aspect, the invention relates to an air-tight, at least partially filled container containing a liquid, aqueous pharmaceutical formulation as defined above, and optionally an inert gas, said container comprising (i) a wall portion and (ii) one or more closure means not constituting part of said wall portion.

DETAILED DESCRIPTION OF THE INVENTION

Figure 1:
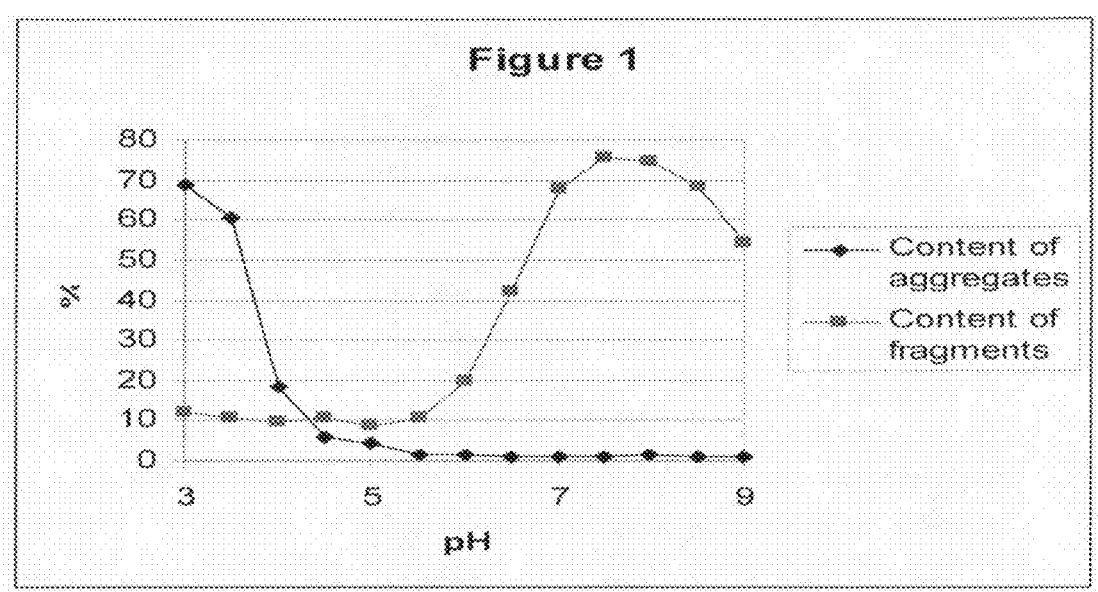
FIG. 1 shows the content of FVII aggregates and FVII fragments in FVII preparations after 3 months of storage at 2-8° C.

As mentioned above, the present invention provides stabilised liquid, aqueous pharmaceutical compositions comprising a factor VII polypeptide. More specifically, the liquid, aqueous pharmaceutical composition comprises a factor VII polypeptide (i), a buffering agent (ii) suitable for keeping pH in the range of from about 4.0 to about 9.0, an agent (iii) selected from the list of: a calcium salt, a magnesium salt, or a mixture thereof; wherein the concentration of (iii) is less than 15 mM, and a ionic strength modifying agent (iv); wherein the ionic strength of the composition is at least about 200 mM.

The compositions according to the present invention are useful as stable and preferably ready-to-use compositions of factor VII polypeptides. Furthermore, it is believed that the principles, guidelines and specific embodiments given herein are equally applicable for bulk storage of Factor VII polypeptides, mutatis mutandis. The compositions are stable for at least six months, and preferably up to 36 months; when stored at temperatures ranging from 2° to 8° C. The compositions are chemically and/or physically stable, in particular chemically stable, when stored for at least 6 months at from 2° to 8° C.

The term "storage-stable" or interchangeable "stable" encompasses a product that is stabilised upon storage at temperatures between 2° C.-8° C. and remains within pre-selected product specifications for a suitable time period— often several months.

The term "stable" is intended to encompass a composition that, after storage for 6 months at 2 to 8° C., retains at least 50% of its initial biological activity as measured by a one-stage clot assay, for example essentially as described in Assay 4 of the present specification. Preferably, the stable composition retains at least 70%, such as 75% or 80% of its initial activity after storage for 6 months at 2 to 8° C.

Furthermore, the term "stable" encompasses a composition that, after storage for at least 6 months at 2 to 8° C., contains less (in %) of at least one of the following degradation products: (i) enzymatic degradation products, (ii) aggregates (dimers, oligomers, polymers), (iii) oxidized forms, or (iv) deamidated forms relative to the amount of corresponding degradation product(s) contained in a solution of reconstituted NovoSeven® product which has been stored under similar conditions for a similar period of time.

The term "physical stability" of Factor VII polypeptides relates to the formation of insoluble and/or soluble aggregates in the form of dimeric, oligomeric and polymeric forms of Factor VII polypeptides as well as any structural deformation and denaturation of the molecule.

The term "chemical stability" is intended to relate to the formation of any chemical change in the Factor VII polypeptides upon storage in solution at accelerated conditions. By example are hydrolysis, deamidation and oxidation as well as enzymatic degradation resulting in formation of fragments of factor VII polypeptides (such as heavy chain degradation), In particular, the sulphur-containing amino acids are prone to oxidation with the formation of the corresponding sulphoxides.

In interesting embodiments of the invention, suitable compositions have a limited increase in the content of enzymatic degradation forms upon storage for at least 6 months at 2-8° C. Interesting embodiments relate to compositions that are stable such that not more than about 25% w/w, such as 20%, 15%, 10%, or not more than about 5% of the initial content of Factor VII polypeptide is converted to enzymatic degradation forms heavy chain fragments upon storage of said composition at 2-8° C. for 6 months.

The term "initial content" relates to the amount of Factor VII polypeptides added to a composition upon preparation of the composition.

The compositions comprise factor VII polypeptides (i), calcium and/or magnesium ions (iii), buffering agents (II), ionic strength modifying agents (iv) and, optionally, other excipients, which further stabilize the factor VII polypeptides, including detergents and tonicity modifiers. The factor VII polypeptides concentration ranges from about 0.1 to about 15 mg/mL.

Factor VII Polypeptide (i):

The terms "human factor VII" or "FVII" denote human factor VII produced by methods including natural source extraction and purification, and by recombinant cell culture systems. Its sequence and characteristics are set forth, for example, in U.S. Pat. No. 4,784,950. The terms likewise cover biologically active human factor VII equivalents, e.g., differing in one or more amino acid(s) in the overall sequence. Furthermore, the terms used in this application are intended to cover substitution, deletion and insertion amino acid variants of factor VII or posttranslational modifications. As used herein, "Factor VII polypeptide" encompasses, without limitation, Factor VII, as well as Factor VII-related polypeptides. Factor VII-related polypeptides include, without limitation, Factor VII polypeptides that have either been chemically modified relative to human Factor VII and/or contain one or more amino acid sequence alterations relative to human Factor VII (i.e., Factor VII variants), and/or contain truncated amino acid sequences relative to human Factor VII (i.e., Factor VII fragments). Such factor VII-related polypeptide s may exhibit different properties relative to human Factor VII, including stability, phospholipid binding, altered specific activity, and the like.

The term "Factor VII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa. The term "Factor VII" is also intended to encompass, without limitation, polypeptides having the amino acid sequence 1-406 of wild-type human Factor VII (as disclosed in U.S. Pat. No. 4,784,950), as well as wild-type Factor VII derived from other species, such as, e.g., bovine, porcine, canine, murine, and salmon Factor VII. It further encompasses natural allelic variations of Factor VII that may exist and occur from one individual to another. Also, degree and location of glycosylation or other post-translation modifications may vary depending on the chosen host cells and the nature of the host cellular environment.

As used herein, "Factor VII-related polypeptides" encompasses, without limitation, polypeptides exhibiting substantially the same or improved biological activity relative to wild-type human Factor VII. These polypeptides include, without limitation, Factor VII or Factor VIIa that has been chemically modified and Factor VII variants into which specific amino acid sequence alterations have been introduced that modify or disrupt the bioactivity of the polypeptide.

It further encompasses polypeptides with a slightly modified amino acid sequence, for instance, polypeptides having a modified N-terminal end including N-terminal amino acid deletions or additions, and/or polypeptides that have been chemically modified relative to human Factor VIIa.

Factor VII-related polypeptides, including variants of Factor VII, exhibiting substantially the same or better bioactivity than wild-type Factor VII, include, without limitation, polypeptides having an amino acid sequence that differs from the sequence of wild-type Factor VII by insertion, deletion, or substitution of one or more amino acids.

Factor VII-related polypeptides, including variants, having substantially the same or improved biological activity relative to wild-type Factor VIIa encompass those that exhibit at least about 25%, such as, e.g., at least about 50%, at least about 75%, at least about 100%, at least about 110%, at least about 120%, or at least about 130% of the specific activity of wild-type Factor VIIa that has been produced in the same cell type, when tested in one or more of a clotting assay, proteolysis assay, or TF binding assay as described in the present specification.

In some embodiments the Factor VII polypeptides are Factor VII-related polypeptides, in particular variants, wherein the ratio between the activity of said Factor VII polypeptide and the activity of native human Factor VIIa (wild-type FVIIa) is at least about 1.25 when tested in the "In Vitro Hydrolysis Assay" (see "Assays", below); in other embodiments, the ratio is at least about 2.0; in further embodiments, the ratio is at least about 4.0. In some embodiments of the invention, the factor VII polypeptides are Factor VII equivalents, in particular variants, wherein the ratio between the activity of said Factor VII polypeptide and the activity of native human Factor VIIa (wild-type FVIIa) is at least about 1.25 when tested in the "In Vitro Proteolysis Assay" (see "Assays", below); in other embodiments, the ratio is at least about 2.0; in further embodiments, the ratio is at least about 4.0; in further embodiments, the ratio is at least about 8.0.

In some embodiments, the Factor VII polypeptide is human Factor VII, as disclosed, e.g., in U.S. Pat. No. 4,784,950 (wild-type Factor VII). In some embodiments, the Factor VII polypeptide is human Factor VIIa. In one series of embodiments, Factor VII polypeptides include polypeptides that exhibit at least about 90%, such as, e.g., at least about 100%, at least about 120%, at least about 140%, or at least about 160%, of the specific biological activity of human Factor VIIa.

In some embodiments, the Factor VII polypeptides have an amino acid sequence that differs from the sequence of wild-type Factor VII by insertion, deletion, or substitution of one or more amino acids.

In one series of embodiments, Factor VII polypeptides include polypeptides that exhibit at least about 70%, preferably at least about 80%, more preferably at least about 90%, and most preferable at least about 95%, of identity with the sequence of wild-type Factor VII as disclosed in U.S. Pat. No. 4,784,950. Amino acid sequence homology/identity is conveniently determined from aligned sequences, using a suitable computer program for sequence alignment, such as, e.g., the ClustalW program, version 1.8, 1999 (Thompson et al., 1994, Nucleic Acid Research, 22: 4673-4680).

Non-limiting examples of Factor VII variants having substantially the same or improved biological activity as wild-type Factor VII include S52A-FVII, S60A-FVII (Lino et al., Arch. Biochem. Biophys. 352: 182-192, 1998); L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII; FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999); FVII variants as disclosed in PCT/DK02/00189; FVII variants exhibiting increased proteolytic stability as disclosed in WO 02/38162 (Scripps Research Institute); FVII variants having a modified Gla-domain and exhibiting an enhanced membrane binding as disclosed in WO 99/20767 (University of Minnesota); FVII variants as disclosed in WO 01/58935 (Maxygen ApS); FVII variants having increased biological activity compared to wild-type FVIIa as disclosed in WO 01/83725, WO 02/22776, WO 02/077218, PCT/DK02/00635, Danish patent application PA 2002 01423, Danish patent application PA 2001 01627; WO 02/38162 (Scripps Research Institute); and FVIIa variants with enhanced activity as disclosed in JP 2001061479 (Chemo-Sero-Therapeutic Res Inst.).

Examples of factor VII or factor VII-related polypeptides include, without limitation, wild-type Factor VII, L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158D/E296V/M298Q/K337A-FVII, L305V/V158T/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/M298Q-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/L305V/V158D/K337A/M298Q-FVII, K316Q/L305V/V158D/E296V/K337A-FVII, K316Q/L305V/V158D/E296V/M298Q/K337A-FVII, K316Q/L305V/V158T/E296V/M298Q/K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/L305V-FVII, F374Y/L305V/K337A-FVII, F374Y/L305V/V158D-FVII, F374Y/L305V/E296V-FVII, F374Y/L305V/M298Q-FVII, F374Y/L305V/V158T-FVII, F374Y/L305V/S314E-FVII, F374Y/K337A/S314E-FVII, F374Y/K337A/V158T-FVII, F374Y/K337A/M298Q-FVII, F374Y/K337A/E296V-FVII, F374Y/K337A/V158D-FVII, F374Y/V158D/S314E-FVII, F374Y/V158D/M298Q-FVII, F374Y/V158D/E296V-FVII, F374Y/V158T/S314E-FVII, F374Y/V158T/M298Q-FVII, F374Y/V158T/E296V-FVII, F374Y/E296V/S314E-FVII, F374Y/S314E/M298Q-FVII, F374Y/E296V/M298Q-FVII, F374Y/L305V/K337A/V158D-FVII, F374Y/

L305V/K337A/E296V-FVII, F374Y/L305V/K337A/ M298Q-FVII, F374Y/L305V/K337A/V158T-FVII, F374Y/ L305V/K337A/S314E-FVII, F374Y/L305V/V158D/ E296V-FVII, F374Y/L305V/V158D/M298Q-FVII, F374Y/ L305V/V158D/S314E-FVII, F374Y/L305V/E296V/ M298Q-FVII, F374Y/L305V/E296V/V158T-FVII, F374Y/ L305V/E296V/S314E-FVII, F374Y/L305V/M298Q/ V158T-FVII, F374Y/L305V/M298Q/S314E-FVII, F374Y/ L305V/V158T/S314E-FVII, F374Y/K337A/S314E/V158T-FVII, F374Y/K337A/S314E/M298Q-FVII, F374Y/K337A/ S314E/E296V-FVII, F374Y/K337A/S314E/V158D-FVII, F374Y/K337A/V158T/M298Q-FVII, F374Y/K337A/ V158T/E296V-FVII, F374Y/K337A/M298Q/E296V-FVII, F374Y/K337A/M298Q/V158D-FVII, F374Y/K337A/ E296V/V158D-FVII, F374Y/V158D/S314E/M298Q-FVII, F374Y/V158D/S314E/E296V-FVII, F374Y/V158D/ M298Q/E296V-FVII, F374Y/V158T/S314E/E296V-FVII, F374Y/V158T/S314E/M298Q-FVII, F374Y/V158T/ M298Q/E296V-FVII, F374Y/E296V/S314E/M298Q-FVII, F374Y/L305V/M298Q/K337A/S314E-FVII, F374Y/ L305V/E296V/K337A/S314E-FVII, F374Y/E296V/ M298Q/K337A/S314E-FVII, F374Y/L305V/E296V/ M298Q/K337A-FVII, F374Y/L305V/E296V/M298Q/ S314E-FVII, F374Y/V158D/E296V/M298Q/K337A-FVII, F374Y/V158D/E296V/M298Q/S314E-FVII, F374Y/ L305V/V158D/K337A/S314E-FVII, F374Y/V158D/ M298Q/K337A/S314E-FVII, F374Y/V158D/E296V/ K337A/S314E-FVII, F374Y/L305V/V158D/E296V/ M298Q-FVII, F374Y/L305V/V158D/M298Q/K337A-FVII, F374Y/L305V/V158D/E296V/K337A-FVII, F374Y/ L305V/V158D/M298Q/S314E-FVII, F374Y/L305V/ V158D/E296V/S314E-FVII, F374Y/V158T/E296V/ M298Q/K337A-FVII, F374Y/V158T/E296V/M298Q/ S314E-FVII, F374Y/L305V/V158T/K337A/S314E-FVII, F374Y/V158T/M298Q/K337A/S314E-FVII, F374Y/ V158T/E296V/K337A/S314E-FVII, F374Y/L305V/ V158T/E296V/M298Q-FVII, F374Y/L305V/V158T/ M298Q/K337A-FVII, F374Y/L305V/V158T/E296V/ K337A-FVII, F374Y/L305V/V158T/M298Q/S314E-FVII, F374Y/L305V/V158T/E296V/S314E-FVII, F374Y/E296V/ M298Q/K337A/V158T/S314E-FVII, F374Y/V158D/ E296V/M298Q/K337A/S314E-FVII, F374Y/L305V/ V158D/E296V/M298Q/S314E-FVII, F374Y/L305V/ E296V/M298Q/V158T/S314E-FVII, F374Y/L305V/ E296V/M298Q/K337A/V158T-FVII, F374Y/L305V/ E296V/K337A/V158T/S314E-FVII, F374Y/L305V/ M298Q/K337A/V158T/S314E-FVII, F374Y/L305V/ V158D/E296V/M298Q/K337A-FVII, F374Y/L305V/ V158D/E296V/K337A/S314E-FVII, F374Y/L305V/ V158D/M298Q/K337A/S314E-FVII, F374Y/L305V/ E296V/M298Q/K337A/V158T/S314E-FVII, F374Y/ L305V/V158D/E296V/M298Q/K337A/S314E-FVII, S52A-Factor VII, S60A-Factor VII; and P11Q/K33E-FVII, T106N-FVII, K143N/N145T-FVII, V253N-FVII, R290N/ A292T-FVII, G291N-FVII, R315N/V317T-FVII, K143N/ N145T/R315N/V317T-FVII; FVII having substitutions, additions or deletions in the amino acid sequence from 233Thr to 240Asn, FVII having substitutions, additions or deletions in the amino acid sequence from 304Arg to 329Cys, and FVII having substitutions, deletions, or additions in the amino acid sequence Ile153-Arg223.

In different embodiments, the factor VII polypeptide is human factor VIIa; recombinant human factor VIIa; a factor VII-related polypeptide; a factor VII sequence variant; or a factor VII polypeptide wherein the activity of the factor VII polypeptide and the activity of native human Factor VIIa (wild-type FVIIa) is at least about 1.25, preferably at least about 2.0, or 4.0, most preferred at least about 8.0, when tested in the "In Vitro Proteolysis Assay" as described in the present specification. In one embodiment, the factor VII polypeptide has a glycosylation different from wild-type human factor VII. In different embodiments, the factor VII polypeptide is present in a concentration of from about 0.1 mg/ml to about 15 mg/ml; from about 0.5 mg/ml to about 10.0 mg/ml; from about 0.5 mg/ml to about 5.0 mg/ml; from about 0.6 mg/ml to about 4.0 mg/ml; from about 1.0 mg/ml to about 4.0 mg/ml; from about 0.1 mg/ml to about 5 mg/ml; from about 0.1 mg/ml to about 4.0 mg/ml; from about 0.1 mg/ml to about 2 mg/ml; or from about 0.1 mg/ml to about 1.5 mg/ml.

Buffering Agent (ii):

In order to render the liquid, aqueous pharmaceutical composition useful for direct parenteral administration to a mammal such as a human, it is normally required that the pH value of the composition is held within certain limits, such as from about 4.0 to about 9.0. To ensure a suitable pH value under the conditions given, the pharmaceutical composition also comprises a buffering agent (ii) suitable for keeping pH in the range of from about 4.0 to about 9.0.

The term "buffering agent" encompasses those agents or combinations of agents which maintain the solution pH in an acceptable range from about 4.0 to about 9.0. These may include, but are not limited to, acids and salt of: MES, PIPES, ACES, BES, TES, HEPES, TRIS, histidine (e.g. L-histidine), imidazole, glycine, glycylglycine, glycinamide, phosphoric acid (e.g. sodium or potassium phosphate), acetic acid (e.g. ammonium, sodium or calcium acetate), lactic acid, glutaric acid, citric acid (e.g. sodium or potassium citrate), tartaric acid, malic acid, maleic acid, and succinic acid. It should be understood that the buffering agent may comprise a mixture of two or more components, wherein the mixture is able to provide a pH value in the specified range. As examples can be mentioned acetic acid and sodium acetate, or acetic acid and histidine, etc.

In one embodiment, the buffering agent (ii) is at least one component selected from the groups consisting of acids and salts of MES, PIPES, ACES, BES, TES, HEPES, TRIS, histidine (e.g. L-histidine), imidazole, glycine, glycylglycine, glycinamide, phosphoric acid (e.g. sodium or potassium phosphate), acetic acid (e.g. ammonium, sodium or calcium acetate), lactic acid, glutaric acid, citric acid (e.g. sodium or potassium citrate), tartaric acid, malic acid, maleic acid, and succinic acid.

In certain embodiments of the invention, the pharmaceutical composition comprises very small amounts of calcium; thus, it is possible to utilise a buffer system based on phosphoric acid, i.e. a phosphate buffer, without undesirable precipitation of calcium phosphates. Thus, in one interesting embodiment, the buffer is a phosphate buffer.

The concentration of the buffering agent is chosen so as to maintain the preferred pH of the solution. In various embodiments, the concentration of the buffering agent is 1-100 mM; 1-50 mM; 1-25 mM; or 2-20 mM.

In one embodiment, the pH of the composition is kept from about 4.0 to about 9.0, such as from about 4.0 to about 8.0, from about 4.0 to about 7.5, from about 4.0 to about 7.0; from about 4.5 to about 7.5; from about 4.5 to about 7.0; from about 5.0 to about 7.5; from about 5.0 and about 7.0; from about 5.0 to about 6.5; from about 5.0 to about 6.0; from about 5.5 to about 7.5; from about 5.5 to about 7.0; from about 5.5 to about 6.5; from about 6.0 to about 7.5; from about 6.5 to about 7.5; or from about 6.0 to about 7.0; from about 6.4 to about 6.6, or about 6.5, from about 5.2 to about 5.7, or about 5.5.

As used herein, pH values specified as "about" are understood to be ±0.1, e.g. about pH 8.0 includes pH 8.0±0.1.

Calcium- and/or Magnesium-Containing Agent (iii):

The liquid, stable pharmaceutical composition comprises an agent (iii) selected from the list of a calcium salt, a magnesium salt, or a mixture thereof. The concentration of the agent (iii) is below 15 mM. In various embodiments, the agent (iii) is present in a concentration of at least about 0.1 µM; at least about 0.5 µM; at least about 1 µM; at least about 5 µM; at least about 10 µM; at least about 50 µM; at least about 100 µM; at least about 1 mM; at least about 2 mM; at least about 5 mM; at least about 10 mM.

In various embodiments, the molar ratio between non-complexed calcium and/or magnesium ions (Ca2+/Mg2+) and FVII polypeptide is: 0.001-750; 0.001-250; 0.001-100; 0.001-10; 0.001-1.0; 0.001-0.5; 0.5-750; 0.5-250; 0.5-100; 0.5-10; 0.5-1.0; 0.001-0.4999; 0.005-0.050.

When used herein, the term "the concentration of non-complexed calcium and/or magnesium ions" is intended to mean the difference between the total concentration of calcium and/or magnesium ions and the concentration of calcium and/or magnesium bound to calcium/magnesium chelators. In this regard, the Factor VII polypeptide is not regarded as a "calcium/magnesium chelator" although calcium and/or magnesium is expected to bind to, or become associated with, the Factor VII polypeptide under certain conditions.

In one embodiment of the present invention, the molar ratio of non-complexed calcium and/or magnesium ions ($Ca^{2+}$/$Mg^{2+}$) to the Factor VII polypeptide is lower than 0.5, e.g. in the range of 0.001-0.499, such as 0.005-0.050, or in the range of 0.000-0.499, such as in the range of 0.000-0.050, or about 0.000. In one embodiment of the present invention, the molar ratio of non-complexed calcium ($Ca^{2+}$) to the Factor VII polypeptide is lower than 0.5, e.g. in the range of 0.001-0.499, such as 0.005-0.050, or in the range of 0.000-0.499, such as in the range of 0.000-0.050, or about 0.000.

In another embodiment, the molar ratio of non-complexed calcium and/or magnesium ions to the Factor VII polypeptide is above 0.5. In another embodiment, the molar ratio of non-complexed calcium ions to the Factor VII polypeptide is above 0.5.

In order to obtain the low relative ratio between calcium and/or magnesium ions ($Ca^{2+}$) and the Factor VII polypeptide, it may be necessary or desirable to remove excess calcium and/or magnesium ions, e.g., by contacting the composition with an ion-exchange material under conditions suitable for removing Ca2+ and/or Mg2+, or to add a calcium/magnesium chelator in order to bind (complex) excess calcium and/or magnesium ions. This is particularly relevant where the ratio between calcium and/or magnesium ions and the Factor VII polypeptide in a solution from a process step preceding the formulation step exceeds the limit stated above. Examples of "calcium/magnesium chelators" include EDTA, citric acid, NTA, DTPA, tartaric acid, lactic acid, malic acid, succinic acid, HIMDA, ADA and similar compounds.

In one embodiment, the calcium salt is selected from the list of: calcium chloride, calcium acetate, calcium gluconate, calcium laevulate, or a mixture thereof.

In one embodiment, the magnesium salt is selected from the list of: magnesium chloride, magnesium acetate, magnesium sulphate, magnesium gluconate, magnesium laevulate, magnesium salts of strong acids, or a mixture thereof.

In a preferred embodiment, the agent (iii) comprises $Ca^{2+}$.

In preferred embodiments, the agent (iii) is selected from the list of: calcium chloride, calcium acetate, magnesium chloride, magnesium acetate, magnesium sulphate, or a mixture thereof; and the ionic strength modifying agent (iv) is sodium chloride or a mixture of sodium chloride and at least one additional ionic strength modifying agent.

Ionic Strength Modifying Agent (iv):

As used herein, the term "ionic strength modifying agent" includes agents, which contribute to the ionic strength of the solution. The agents include, but are not limited to, neutral salts, e.g., sodium chloride or potassium chloride; amino acids; small peptides (e.g., having from 2 to 5 amino acid residues such as, e.g., glycylglycine), or a mixture of at least two of said modifying agents. The "ionic strength modifying agent" may also be a mixture of two or more such agents that in combination are able to modify the ionic strength to a level as defined in the present invention. Preferred agents are sodium chloride or a mixture of sodium chloride with one or more small peptides or amino acids. The ionic strength modifying agent(s) is/are present in a concentration sufficient to elevate the ionic strength of the solution to at least 200 mM (calculated on the basis of millimolar concentrations of agents). The ionic strength modifying agents may, e.g., without limitation, each be present in a concentration of at least about 5 mM, 10 mM, 20 mM, 50 mM, 100 mM, 200 mM, 400 mM, 800 mM, 1000 mM, 1200 mM, 1500 mM, 1800 mM, 2000 mM, or at least 2200 mM.

The term "ionic strength" is the ionic strength of the solution ($\mu$) which, in the present context, is defined by the equation: $\mu = \frac{1}{2}\Sigma C_i(Z_i^2)$, where $\mu$ is the ionic strength, $C_i$ is the molar concentration of an ion, and $Z_i$ is the charge (+ or −) of that ion (see, for example, Solomon, Journal of Chemical Education, 78(12):1691-92, 2001; James Fritz and George Schenk: Quantitative Analytical Chemistry, 1979).

In various embodiments of the invention, the ionic strength of the composition is at least 200 mM, such as at least 250 mM, at least 300 mM, at least 400 mM, at least 500 mM, at least 650 mM, at least 800 mM, at least 1000 mM, at least 1200 mM, at least 1600 mM, at least 2000 mM, at least 2400 mM, at least 2800 mM, or at least 3200 mM (ionic strength calculations based on millimolar (mM) concentrations of components).

In different embodiments, the ionic strength modifying agent (iv) is selected from the list of: a neutral salt, e.g., sodium chloride; an amino acid; or a small peptide, or a mixture of at least two of said modifying agents. In one embodiment the ionic strength modifying agent comprises sodium chloride. In another embodiment the ionic strength modifying agent is sodium chloride By "neutral salt" is meant a salt that is neither an acid nor a base when dissolved in aqueous solution. Examples include sodium chloride or potassium chloride.

In important embodiments, the pharmaceutical composition is adapted to subcutaneous, intramuscular or intravenous injection according to methods known in the art. The possibly high concentration of salts may be disadvantageous for certain groups of patients. The present invention therefore also provides a prior-to-use method for lowering the salt concentration in a liquid, aqueous pharmaceutical composition, wherein said method comprises the step of contacting the liquid, aqueous pharmaceutical composition defined herein with an ion-exchange material, a suitable material for desalting, and/or the step of diluting the composition.

The ion-exchange material is preferably contained in a sterile container, e.g. in a glass or plastic cartridge.

It is envisaged that the liquid, aqueous pharmaceutical composition is contacted with the ion-exchange material, e.g. by passage through a cartridge containing the ion-exchange material, immediately prior to use. In a particular embodiment, it is envisaged that the cartridge is an integral part of a syringe assembly.

Other Ingredients:

Tonicity Modifier:

As used herein, the term "tonicity modifier" includes agents, which contribute to the osmolality of the solution. Tonicity modifiers include, but are not limited to, amino acids; small peptides (e.g., having from 2 to 5 amino acid residues); neutral salts; mono- or disaccharides; polysaccharides; sugar alcohols, or a mixture of at least two of said modifiers. Examples of tonicity modifiers include, but are not limited to, sodium chloride, potassium chloride, sodium citrate, sucrose, glucose, glycylglycine, trehalose, and mannitol. Normally, the modifiers are present at a concentration of from about 1 to about 500 mM; from about 1 to about 300 mM; from about 10 to about 200 mM; or from about 20 to about 150 mM, depending on the other ingredients present. Neutral salts such as, e.g., sodium chloride or potassium chloride may be used.

In one embodiment, the pharmaceutical composition comprises a tonicity modifying agent (v). In one embodiment the tonicity modifying agent (v) is selected from the list of: a neutral salt; a mono-, di- or polysaccharide; a sugar alcohol; an amino acid; or a small peptide, or a mixture of at least two of said modifying agents.

Surfactant

Optionally, the compositions may also contain a surfactant or detergent (vi). "Surfactants" or "detergents" generally include those agents which protect the protein from air/solution interface induced stresses and solution/surface induced stresses (e.g., resulting in protein aggregation). The detergent is preferably a non-ionic detergent including, without limitation, polysorbates (e.g. Tween®), such as polysorbate 20 or 80; polyoxyethylene alkyl ethers or poloxamers, such as poloxamer 188 or 407, (e.g., Pluronic® polyols) and other ethylene/polypropylene block polymers, or polyethyleneglycol (PEG) such as PEG8000. The amount of surfactant present ranges from about 0.005 to about 2.0%.

In various embodiments, the non-ionic surfactant is a polysorbate or a poloxamer or a polyoxyethylene alkyl ether; preferably poloxamer 188 or poloxamer 407, or polysorbate 20 or polysorbate 80, or polyoxy 23 lauryl ether.

Antioxidants

Optionally, the composition may include an antioxidant (vii). Antioxidants include, but are not limited to, ascorbic acid, cysteine, homocysteine, cystine, cysstathionine, methionine, gluthatione, and other peptides containing cysteine or methionine, in particular peptides with 2 to 5 amino acid residues wherein at least one of the residues is a methionine or cysteine residue; methionine, in particular L-methionine, is preferred. The antioxidant is included at a concentration of 0.1 to 5 mg/ml, such as 0.1 to 4, 0.1 to 3, 0.1 to 2, or 0.5 to 2 mg/ml.

In one embodiment the antioxidant (vii) is selected from the list of: L- or D-methionine, a methionine analogue, a methionine-containing peptide, a methionine-homologue, ascorbic acid, cysteine, homocysteine, gluthatione, cystine, and cysstathionine. In one embodiment, the antioxidant is L-methionine.

Preservative:

A preservative (viii) may also be included in the composition to retard microbial growth and thereby allow "multiple use" packaging of the FVII polypeptides. Preservatives include phenol, benzyl alcohol, orto-cresol, meta-cresol, para-cresol, methyl paraben, propyl paraben, benzalconium chloride, and benzethonium chloride. The preservative is normally included at a concentration of 0.1 to 20 mg/ml depending on pH range and type of preservative.

Optionally, the composition may also include an agent capable of inhibiting deamidation and/or isomerization.

As used herein, amounts specified are understood to be ± about 10%, e.g., about 50 mM includes 50 mM±5 mM; e.g., 4% includes 4%±0.4%, etc.

Percentages are (weight/weight) both when referring to solids dissolved in solution and liquids mixed into solutions. For example, for Tween, it is the weight of 100% stock/weight of solution.

The term "isotonic" means "isotonic with serum", i.e., at about 300±50 milliosmol/kg. The tonicity is meant to be a measure of osmolality of the solution prior to administration. The term "hypertonic" is meant to designate levels of osmolality above the physiological level of serum, such as levels above 300±50 milliosmol/kg.

In one embodiment, the composition is isotonic; in another, it is hypertonic. In one embodiment, the composition is formulated for pharmaceutical administration. In one embodiment, the composition is stable for storage for at least 6 months at 2-8° C.

Methods of Use:

The compositions or preparations of the present invention may be used to treat any Factor VII-responsive syndrome, such as, e.g., bleeding disorders, including, without limitation, those caused by clotting factor deficiencies (e.g., haemophilia A and B or deficiency of coagulation factors XI or VII); by thrombocytopenia or von Willebrand's disease, or by clotting factor inhibitors, or excessive bleeding from any cause. The preparations may also be administered to patients in association with surgery or other trauma or to patients receiving anticoagulant therapy.

The term "pharmaceutically effective amount" or "effective amount" is the effective dose to be determined by a qualified practitioner, who may titrate dosages to achieve the desired response. Factors for consideration of dose will include potency, bioavailability, desired pharmacokinetic/pharmacodynamic profiles, condition of treatment, patient-related factors (e.g. weight, health, age, etc.), presence of co-administered medications (e.g., anticoagulants), time of administration, or other factors known to a medical practitioner.

The term "treatment" is defined as the management and care of a subject, e.g. a mammal, in particular a human, for the purpose of combating the disease, condition, or disorder and includes the administration of a factor VII polypeptide to prevent the onset of the symptoms or complications, or alleviating the symptoms or complications, or eliminating the disease, condition, or disorder. Pharmaceutical compositions according to the present invention containing a factor VII polypeptide may be administered parenterally to subjects in need of such a treatment. Parenteral administration may be performed by subcutaneous, intramuscular or intravenous injection by means of a syringe, optionally a pen-like syringe. Alternatively, parenteral administration can be performed by means of an infusion pump.

Factor VIIa concentration is conveniently expressed as mg/mL or as IU/mL, with 1 mg usually representing 43000-56000 IU or more.

In different embodiments, the syndrome is selected from the group consisting of haemophilia A, haemophilia B, Factor XI deficiency, Factor VII deficiency, thrombocytopenia, von Willebrand's disease, presence of a clotting factor inhibitor, surgery, intra cerebral haemorrhage, trauma, stem cell transplantation, liver disease, dilution coagulopathy, upper gastointestinal bleedings, and anticoagulant therapy.

General Methods

Assays Suitable for Determining Biological Activity of Factor VII Polypeptides:

The biological activity of Factor VIIa in blood clotting derives from its ability to (i) bind to tissue factor (TF) and (ii) catalyze the proteolytic cleavage of Factor IX or Factor X to produce activated Factor IX or X (Factor IXa or Xa, respectively).

For purposes of the invention, biological activity of Factor VII polypeptides ("Factor VII biological activity") may be quantified by measuring the ability of a preparation to promote blood clotting using Factor VII-deficient plasma and thromboplastin, as described, e.g., in U.S. Pat. No. 5,997,864 or WO 92/15686. In this assay, biological activity is expressed as the reduction in clotting time relative to a control sample and is converted to "Factor VII units" by comparison with a pooled human serum standard containing 1 unit/ml Factor VII activity. Alternatively, Factor VIIa biological activity may be quantified by Measuring the ability of Factor VIIa or a Factor VII-related polypeptide to produce activated Factor X (Factor Xa) in a system comprising TF embedded in a lipid membrane and Factor X. (Persson et al., J. Biol. Chem. 272:19919-19924, 1997);

Measuring Factor X hydrolysis in an aqueous system ("In Vitro Proteolysis Assay", see below);

Measuring the physical binding of Factor VIIa or a Factor VII-related polypeptide to TF using an instrument based on surface plasmon resonance (Persson, FEBS Letts. 413:359-363, 1997);

Measuring hydrolysis of a synthetic substrate by Factor VIIa and/or a Factor VII-related polypeptide ("In Vitro Hydrolysis Assay", see below);

Measuring generation of thrombin in a TF-independent in vitro system.

Factor VII polypeptides useful in accordance with the present invention may be selected by suitable assays that can be performed as simple preliminary in vitro tests. Thus, the present specification discloses a simple test (entitled "In Vitro Hydrolysis Assay") for the activity of Factor VII polypeptides.

In Vitro Hydrolysis Assay (Assay 1)

Native (wild-type) factor VIIa and Factor VII polypeptide (both hereafter referred to as "factor VIIa") may be assayed for specific activities. They may also be assayed in parallel to directly compare their specific activities. The assay is carried out in a microtiter plate (MaxiSorp, Nunc, Denmark). The chromogenic substrate D-Ile-Pro-Arg-p-nitroanilide (S-2288, Chromogenix, Sweden), final concentration 1 mM, is added to factor VIIa (final concentration 100 nM) in 50 mM Hepes, pH 7.4, containing 0.1 M NaCl, 5 mM CaCl2 and 1 mg/ml bovine serum albumin. The absorbance at 405 nm is measured continuously in a SpectraMax™ 340 plate reader (Molecular Devices, USA). The absorbance developed during a 20-minute incubation, after subtraction of the absorbance in a blank well containing no enzyme, is used to calculate the ratio between the activities of Factor VII polypeptide and wild-type factor VIIa:

Ratio=($A$405 nm Factor VII polypeptide)/($A$405 nm factor VIIa wild-type).

Based thereon, Factor VII polypeptides with an activity lower than, comparable to, or higher than native factor VIIa may be identified, such as, for example, Factor VII polypeptides where the ratio between the activity of the Factor VII polypeptide and the activity of native factor VII (wild-type FVII) is about, versus above 1.0.

The activity of the Factor VII polypeptides may also be measured using a physiological substrate such as factor X ("In Vitro Proteolysis Assay"), suitably at a concentration of 100-1000 nM, where the factor Xa generated is measured after the addition of a suitable chromogenic substrate (eg. S-2765). In addition, the activity assay may be run at physiological temperature.

In Vitro Proteolysis Assay (Assay 2)

Native (wild-type) Factor VIIa and Factor VII polypeptide (both hereafter referred to as "Factor VIIa") are assayed in parallel to directly compare their specific activities. The assay is carried out in a microtiter plate (MaxiSorp, Nunc, Denmark). Factor VIIa (10 nM) and Factor X (0.8 microM) in 100 microL 50 mM Hepes, pH 7.4, containing 0.1 M NaCl, 5 mM CaCl2 and 1 mg/ml bovine serum albumin, are incubated for 15 min. Factor X cleavage is then stopped by the addition of 50 microL 50 mM Hepes, pH 7.4, containing 0.1 M NaCl, 20 mM EDTA and 1 mg/ml bovine serum albumin. The amount of Factor Xa generated is measured by addition of the chromogenic substrate Z-D-Arg-Gly-Arg-p-nitroanilide (S-2765, Chromogenix, Sweden), final concentration 0.5 mM. The absorbance at 405 nm is measured continuously in a SpectraMax™ 340 plate reader (Molecular Devices, USA). The absorbance developed during 10 minutes, after subtraction of the absorbance in a blank well containing no FVIIa, is used to calculate the ratio between the proteolytic activities of Factor VII polypeptide and wild-type Factor VIIa:

Ratio=($A$405 nm Factor VII polypeptide)/($A$405 nm Factor VIIa wild-type).

Based thereon, Factor VII polypeptide with an activity lower than, comparable to, or higher than native factor VIIa may be identified, such as, for example, Factor VII polypeptides where the ratio between the activity of the Factor VII polypeptide and the activity of native factor VII (wild-type FVII) is about, versus above 1.0.

The ability of factor VIIa or Factor VII polypeptides to generate thrombin can also be measured in an assay (Assay 3) comprising all relevant coagulation factors and inhibitors at physiological concentrations (minus factor VIII when mimicking hemophilia A conditions) and activated platelets (as described on p. 543 in Monroe et al. (1997) Brit. J. Haematol. 99, 542-547, which is hereby incorporated as reference)

The activity of the Factor VII polypeptides may also be measured using a one-stage clot assay (Assay 4) essentially as described in WO 92/15686 or U.S. Pat. No. 5,997,864. Briefly, the sample to be tested is diluted in 50 mM Tris (pH 7.5), 0.1% BSA and 100 µl is incubated with 100 µl of Factor VII deficient plasma and 200 µl of thromboplastin C containing 10 mM $Ca^{2+}$. Clotting times are measured and compared to a standard curve using a reference standard or a pool of citrated normal human plasma in serial dilution.

Preparation and Purification of Factor VII Polypeptides:

Human purified Factor VIIa suitable for use in the present invention is preferably made by DNA recombinant technology, e.g. as described by Hagen et al., Proc. Natl. Acad. Sci. USA 83: 2412-2416, 1986, or as described in European Patent No. 200.421 (ZymoGenetics, Inc.).

Factor VII may also be produced by the methods described by Broze and Majerus, J. Biol. Chem. 255 (4): 1242-1247, 1980 and Hedner and Kisiel, J. Clin. Invest. 71: 1836-1841, 1983. These methods yield Factor VII without detectable amounts of other blood coagulation factors. An even further purified Factor VII preparation may be obtained by including an additional gel filtration as the final purification step. Factor VII is then converted into activated factor VIIa by known means, e.g. by several different plasma proteins, such as factor XIIa, IX a or Xa. Alternatively, as described by Bjoern et al. (Research Disclosure, 269 September 1986, pp. 564-565), factor VII may be activated by passing it through an ion-exchange chromatography column, such as Mono Q® (Pharmacia fine Chemicals) or the like, or by autoactivation in solution.

Factor VII-related polypeptides may be produced by modification of wild-type Factor VII or by recombinant technology. Factor VII-related polypeptides with altered amino acid sequence when compared to wild-type Factor VII may be produced by modifying the nucleic acid sequence encoding wild-type factor VII either by altering the amino acid codons or by removal of some of the amino acid codons in the nucleic acid encoding the natural factor VII by known means, e.g. by site-specific mutagenesis.

It will be apparent to those skilled in the art that substitutions can be made outside the regions critical to the function of the factor VIIa molecule and still result in an active polypeptide. Amino acid residues essential to the activity of the Factor VII polypeptide, and therefore preferably not subject to substitution, may be identified according to procedures known in the art, such as site-directed mutagenesis or alanine-scanning mutagenesis (see, e.g., Cunningham and Wells, 1989, Science 244: 1081-1085). In the latter technique, mutations are introduced at every positively charged residue in the molecule, and the resultant mutant molecules are tested for coagulant, respectively cross-linking activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, Science 255: 306-312; Smith et al., 1992, Journal of Molecular Biology 224: 899-904; Wlodaver et al., 1992, FEBS Letters 309: 59-64).

The introduction of a mutation into the nucleic acid sequence to exchange one nucleotide for another nucleotide may be accomplished by site-directed mutagenesis using any of the methods known in the art. Particularly useful is the procedure that utilizes a super coiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI, which is specific for methylated and hemi-methylated DNA to digest the parental DNA template and to select for mutation-containing synthesized DNA. Other procedures known in the art for creating, identifying and isolating variants may also be used, such as, for example, gene shuffling or phage display techniques.

Separation of polypeptides from their cell of origin may be achieved by any method known in the art, including, without limitation, removal of cell culture medium containing the desired product from an adherent cell culture; centrifugation or filtration to remove non-adherent cells; and the like.

Optionally, Factor VII polypeptides may be further purified. Purification may be achieved using any method known in the art, including, without limitation, affinity chromatography, such as, e.g., on an anti-Factor VII antibody column (see, e.g., Wakabayashi et al., J. Biol. Chem. 261:11097, 1986; and Thim et al., Biochem. 27:7785, 1988); hydrophobic interaction chromatography; ion-exchange chromatography; size exclusion chromatography; electrophoretic procedures (e.g., preparative isoelectric focusing (IEF), differential solubility (e.g., ammonium sulfate precipitation), or extraction and the like. See, generally, Scopes, Protein Purification, Springer-Verlag, New York, 1982; and Protein Purification, J. C. Janson and Lars Ryden, editors, VCH Publishers, New York, 1989. Following purification, the preparation preferably contains less than about 10% by weight, more preferably less than about 5% and most preferably less than about 1%, of non-Factor VII polypeptides derived from the host cell.

Factor VII polypeptides may be activated by proteolytic cleavage, using Factor XIIa or other proteases having trypsin-like specificity, such as, e.g., Factor IXa, kallikrein, Factor Xa, and thrombin. See, e.g., Osterud et al., Biochem. 11:2853 (1972); Thomas, U.S. Pat. No. 4,456,591; and Hedner et al., J. Clin. Invest. 71:1836 (1983). Alternatively, Factor VII polypeptides may be activated by passing it through an ion-exchange chromatography column, such as Mono Q® (Pharmacia) or the like, or by autoactivation in solution. The resulting activated Factor VII polypeptide may then be formulated and administered as described in the present application.

The following examples illustrate practice of the invention. These examples are for illustrative purposes only and are not intended in any way to limit the scope of the invention claimed.

EXAMPLES

Example 1

Analytical Methods Used in Determining Stability Indicating Parameters:

A. Determination of Oxidised forms by Reverse Phase HPLC (RP-HPLC):

HPLC Column: 4.5×250 mm column packed with butyl-bonded silica with a particle size of 5 µm and pore size 300 Å. Column temperature: 70° C. Eluent A: water 99.9% v/v and trifluoracetic acid 0.1% v/v. Eluent B: acetonitrile 80% v/v. trifluoracetic acid 0.09% v/v and water 19.91% v/v. The column was eluted with a linear gradient from X % B to (X+13) % B in 30 minutes. Flow rate: 1.0 ml/min. Detection: 214 nm.

The oxidised forms are methionine sulfoxides of Factor VII Polypeptides. For example the two main derivatives of FVII are Met(O)298 FVII and Met(O)306 FVII.

The content of oxidised forms is expressed as the percentage of the initial amount of Factor VII in the composition upon preparation that is recovered as oxidised forms of Factor VII.

B. Determination of aggregates of Factor VII polypeptides by High Performance Gel Permeation Chromatography (GP-HPLC).

GP-HPLC was run on a Waters Protein Pak 300 SW column. 7.5×300 mm. using 0.2 M ammoniumsulfat pH 7.0 containing 50% isopropanol as the mobile phase. Flow rate: 0.5 ml/min and detection: 215 nm.

The content of aggregates is expressed as the percentage of the initial amount of Factor VII in the composition upon preparation that is recovered as dimeric, oligomeric and polymeric forms of Factor VII.

Example 2

Composition Preparation

In general, aqueous FVIIa composition samples for analysis in these experimental examples were prepared from a purified bulk solution by buffer exchange on a gel filtration column. Composition additives were either contained in the elution buffer in their final ratios or added to the eluate. The resulting solution was sterile filtered using a sterilized membrane filter (0.2 micron pore size or equivalent) and filled into sterile glass vials, stoppered and sealed with butyl rubber stoppers and aluminum flip-off type caps.

Example 3

Effect of pH on the Chemical/Physical Stability (I) Vials of the rFVIIa aqueous composition containing 1.4 mg rFVIIa/mL, 50 mM Sodium chloride, 10 mM Calcium chloride and a mixture of 10 mM glycylglycine, acetate and histidine adjusted to pH 3, 3.5, 4.0, 4.5, 5.0, 5.5, 6.0, 6.5, 7.0, 7.5, 8.0, 8.5, and 9.0 were incubated at either a temperature of 2-8° C., or at elevated storage temperatures of 30° C., and then removed at various time points and assayed for changes in pH and the chemical stability was determined by RP-HPLC and GP-HPLC.

After storage at 2-8° C. for up to three months the aqueous compositions showed insignificant changes in pH. Non-denaturing size exclusion HPLC performed on samples stored for up to three months at 2-8° C. showed no significant aggregation of the drug product at pH values 5.5 (FIG. 1). RP-HPLC performed on these samples showed no significant increase in the fragmentation or oxidation of the protein in the pH range 4.5-5.5. FIG. 1 shows data after 3 months of storage at 2-8° C. The initial content of aggregates was approximately 0.5% and the initial content of fragments was approximately 9%.

(II) Vials of the rFVIIa aqueous composition containing 1.4 mg rFVIIa/mL, 200 mM Sodium chloride, 10 mM Calcium chloride and a mixture of 10 mM glycylglycine, acetate and histidine adjusted to pH 3, 3.5, 4.0, 4.5, 5.0, 5.5, 6.0, 6.5, 7.0, 7.5, 8.0, 8.5, and 9.0 are incubated at either a temperature of 2-8° C., or at elevated storage temperatures of 30° C., and then removed at various time points and assayed for changes in pH; the chemical stability is determined by RP-HPLC and GP-HPLC.

After storage at 2-8° C. for up to three months, it is contemplated that the aqueous compositions will show insignificant changes in pH. It is further contemplated that non-denaturing size exclusion HPLC performed on samples stored for up to three months at 2-8° C. will show no significant aggregation of the drug product at pH values 5.5. It is further contemplated that RP-HPLC performed on these samples will show no significant increase in the fragmentation or oxidation of the protein in the pH range 4.5-5.5.

Example 4

Physical Stability of Aqueous Compositions Containing Various Detergents

Twelve different compositions were prepared. The compositions were:

| | |
|---|---|
| rFVIIa | 0.75 mg/ml |
| NaCl | 2.92 mg/ml |
| CaCl2, 2H2O | 1.47 mg/ml |
| Glycylglycine | 1.32 mg/ml |
| Detergent/solubiliser | x mg/ml |
| pH | 5.5 |

The concentrations of the detergents/solubilisers tested are stated in the table below.

The compositions were prepared from a liquid bulk solution of rFVIIa. Stock solutions of the detergents/solubilisers were prepared in buffers containing NaCl, CaCl2, 2H2O, and glycylglycine in the concentrations stated above. The rFVIIa bulk and the detergent solutions were mixed, and the pH in the solutions was adjusted to 5.5. The compositions were filtered (0.2 μm) and filled in vials (1 ml solution per vial).

The appearance of the compositions was determined by visual inspection and the absorbance of the composition at 400 nm was determined. Subsequently, the vials were shaken for 19 hours (800/min) at room temperature. After completing the shaking, the appearance and the absorbance at 400 nm was determined. The results are listed in the table below.

| Detergent type | Conc. (mg/ml) | Appearance Before | Appearance After | Absorbance (400 nm) Before | Absorbance (400 nm) After | Absorbance (400 nm) Increase |
|---|---|---|---|---|---|---|
| None (reference) | — | Few part. | Very turbid | 0.0085 | 1.4386 | 1.4301 |
| Tween ® 80 | 0.1 | Very few part. | Clear, few part. | 0.0044 | 0.0036 | −0.0008 |
| Tween ® 20 | 0.1 | Very few part. | Clear, few part. | 0.0039 | 0.0101 | 0.0062 |
| Poloxamer 188 | 1.0 | Very few part. | Clear, few part. | 0.0063 | 0.0027 | −0.0036 |
| Pluronic ® F127 | 1.0 | Very few part. | Clear, few part. | 0.0000 | 0.0048 | 0.0048 |
| Polyethylenglycol 400 | 0.1 | Very few part. | Turbid | 0.0076 | 1.5708 | 1.5632 |
| Polyethylenglycol 4000 | 0.5 | Few part. | Very turbid | 0.0108 | 1.6624 | 1.6516 |
| Brij ® 35 | 0.1 | Very few part. | Clear, few part. | 0.0028 | 0.0015 | −0.0013 |
| Myrj ® 59 | 0.1 | Very few part. | Clear, few part. | 0.0002 | 0.1110 | 0.1108 |
| Myrj ® 52 | 0.1 | Very few part. | Clear, few part. | 0.0009 | 0.9390 | 0.9381 |

-continued

| Detergent type | Conc. (mg/ml) | Appearance Before | Appearance After | Absorbance (400 nm) Before | Absorbance (400 nm) After | Increase |
|---|---|---|---|---|---|---|
| LPCM | 0.1 | Very few part. | Clear, few part. | 0.0026 | 0.0012 | −0.0014 |
| Glycerol | 1.0 | Very few part. | Turbid | 0.0040 | 1.4064 | 1.4024 |

"part." = "particles"

The results show that the reference (without addition of any detergent/solubiliser) becomes visually turbid when shaken and a significant increase is observed in the absorbance at 400 nm. Addition of Tween® 20 (=polysorbate 20), Tween® 80 (=polysorbate 80), Poloxamer 188, Pluronic® F127 (=poloxamer 407), Brij® 35 (=polyoxyl 23 lauryl ether), and LPCM (=α-lysophasphatidylcholine myristoyl) almost completely prevented increase in turbidy and absorbance, while a slighter increase in turbidity (as compared to the reference) was observed for Myrj® 59 (=polyoxyl 100 stearate) and Myrj® 52 (=polyoxyl 40 stearate).

Example 5

Chemical Stability of Aqueous Compositions Containing Methionine as Antioxidant (I) Three different compositions were prepared. The compositions were:

| rFVIIa | 0.75 mg/ml |
|---|---|
| NaCl | 2.92 mg/ml |
| CaCl2, 2H2O | 1.47 mg/ml |
| Glycylglycine | 1.32 mg/ml |
| Methionine | 0 or 0.25 or 1.0 mg/ml |
| pH | 6.5 |

The compositions were prepared from a liquid bulk solution of rFVIIa. The methionine was dissolved in buffers containing NaCl, CaCl$_2$, 2H$_2$O, and glycylglycine in the concentrations stated above. The rFVIIa bulk and the methionine solutions were mixed, and the pH in the solutions was adjusted to 6.5. The compositions were filtered (0.2 μm) and filled in vials (1 ml solution per vial). The vials were stored at 5° C., 25° C. and 40° C. Samples were withdrawn and analysed for content of oxidized forms (by RP-HPLC) at the time point stated in the table below. The table shows the content of oxidised forms (in %).

| Methionine (mg/ml) | Time zero | 25° C. 14 days | 40° C. 14 days | 25° C. 28 days | 40° C. 28 days | 5° C. 90 days |
|---|---|---|---|---|---|---|
| 0 (reference) | 2.4 | 4.4 | 7.5 | 4.4 | 12.8 | 3.1 |
| 0.25 | 1.7 | 2.4 | 5.3 | 2.8 | 9.9 | 1.9 |
| 1.0 | 1.6 | 2.3 | 5.0 | 2.6 | 9.6 | 1.3 |

The results show that addition of methionine slows down the oxidation rate in the composition.

(II) Three different compositions are prepared. The compositions are:

| rFVIIa | 0.75 mg/ml |
|---|---|
| NaCl | 11.68 mg/ml (200 mM) |
| CaCl2, 2H2O | 1.47 mg/ml |
| Glycylglycine | 1.32 mg/ml |
| Methionine | 0 or 0.25 or 1.0 mg/ml |
| pH | 6.5 |

The compositions are prepared from a liquid bulk solution of rFVIIa. The methionine is dissolved in buffers containing NaCl, CaCl$_2$, 2H$_2$O, and glycylglycine to obtain the concentrations stated above. The rFVIIa bulk and the methionine solutions are mixed, and the pH in the solutions is adjusted to 6.5. The compositions are filtered (0.2 μm) and filled in vials (1 ml solution per vial). The vials are stored at 5° C., 25° C. and 40° C. Samples are withdrawn and analysed for content of oxidized forms (in %) (by RP-HPLC) at the time point stated in the table above.

It is contemplated that the results will show that addition of methionine slows down the oxidation rate in the composition.

Example 6

Chemical Stability of Aqueous Compositions Containing Sodium Chloride

Four different compositions are prepared. The compositions are:

| rFVIIa | 1.0 mg/ml |
|---|---|
| NaCl | 2.92 mg/ml (50 mM; Composition 1) |
| | 11.68 mg/ml (200 mM; Composition 2) |
| | 23.36 mg/ml (400 mM; Composition 3) |
| | 46.42 mg/ml (800 mM; Composition 4) |
| | 58.4 mg/ml (1000 mM; Composition 5) |
| CaCl2, 2H2O | 1.47 mg/ml (10 mM) |
| Glycylglycine | 1.32 mg/ml |
| pH | 7.0 |

The compositions are prepared from a liquid bulk solution of rFVIIa. Calcium chloride is dissolved in buffers containing NaCl and glycylglycine to give the concentrations stated above after mixing with rFVIIa bulk. After mixing, the pH in the solutions are adjusted to 7.0. The compositions are filtered (0.2 μm) and filled in vials (1 ml solution per vial). The vials are stored at 5° C.

For each formulation the activity of factor VII (IU/ml) are determined by clot assay at 0 months (measuring IU/ml) and after 3 months of storage at 5° C. (measuring IU/ml). It is contemplated that the clot assays will show that the compositions containing at least 200 mM of sodium chloride (Compositions 2-5) have a higher clotting activity after 3 months of storage (higher IU/ml) compared to Composition 1.

Heavy Chain Degradation

For each formulation the formation of heavy chain fragments are measured by RP-HPLC as described in example 1. The results (as % fragments) are measured at 0 months as well as during storage at 5° C. and 30° C., respectively; The contents of heavy chain fragments (as % fragments) are measured at 1, 2, 3, and 6 months.

It is contemplated that the measurements will show that the formation of heavy degradation fragments in Compositions 2-5 (as % fragments) are less than the formation of fragments in Composition 1.

Example 7

Chemical Stability of Aqueous Compositions Containing Sodium Chloride

Four different compositions were prepared. The compositions were:

| | |
|---|---|
| rFVIIa | 1.0 mg/ml |
| NaCl | 0 mg/ml (0 mM; Composition 1) |
| | 29.2 mg/ml (500 mM; Composition 2) |
| | 43.8 mg/ml (750 mM; Composition 3) |
| | 58.4 mg/ml (1000 mM; Composition 4) |
| $CaCl_2$, $2H_2O$ | 1.47 mg/ml (10 mM) |
| PIPES-di-Na | 17.3 mg/ml (50 mM) |
| pH | 6.5 |

The compositions were prepared from a liquid bulk solution of rFVIIa. The liquid bulk solution was desalted into the desired compositions using PD-10 columns from Pharmacia. After desalting, the pH in the solutions were adjusted to 6.5. The compositions were filtered (0.22 μm) and filled in cartridges. The cartridges were stored at 5° C. For each formulation the content of heavy chain fragments (%) were measured by RP-HPLC (example 1) at various time points, data are listed in the table below.

| | Content of heavy chain fragments (%) | | | | |
|---|---|---|---|---|---|
| | Storage time at 5° C. (months) | | | | |
| Composition | 0 | ½ | 1 | 2 | 3 |
| 1 | 11.6 | 15.6 | 19.0 | 24.1 | 27.8 |
| 2 | 12.2 | 13.2 | 15.3 | 16.7 | 18.9 |
| 3 | 12.2 | 13.2 | 14.6 | 16.0 | 18.1 |
| 4 | 12.2 | 13.0 | 14.4 | 15.3 | 17.1 |

It is seen that by increasing the concentration of NaCl the formation of heavy chain fragments was decreased.

For formulation 1 and 4 the clot activity of factor VII (IU/ml) was determined at various time points. In the table below the clot activity at the various time points has been listed relative to the time point zero value (=100%).

| | Clot activity | | |
|---|---|---|---|
| | Storage time at 5° C. (months) | | |
| Composition | 0 | 3 | 11 |
| 1 | 100% | 85% | 67%* |
| 4 | 100% | 88% | 82% |

*8 months value

It is seen that the clot activity was higher in composition 4 containing NaCl.

Example 8

Effect of Ionic Strength on Chemical Stability

Four formulations were prepared by mixing purified rFVIIa bulk solution with stock solutions containing excipients. In the formulations the contents of NaCl and CaCl2 were varied as shown in the table below

| Formulation | mg/ml NaCl | mg/ml $CaCl_2$ |
|---|---|---|
| A | 2.92 | 1.47 |
| B | 58.4 | 1.47 |

Furthermore, all formulations contained 1 mg/ml rFVIIa, 10 mM Glycylglycine, 10 mM Sodium acetate, and 10 mM L-Histidine. The pH was adjusted to 7.0 in all formulations.

The formulations were stored at 30° C. and the contents of heavy chain fragments were measured by RP-HPLC (example 1). The results (as % fragments) are listed in the table below.

| Formulation | 0 month | 1 months | 2 months | 3 months |
|---|---|---|---|---|
| A | 12.7 | 31.3 | 39.1 | 43.6 |
| B | 9.8 | 19.1 | 23.2 | 26.7 |

The results show that a higher ionic strength (here obtained by addition of NaCl) resulted in a decreased formation of heavy chain fragments during storage.

The invention claimed is:

1. A liquid, aqueous composition comprising:
   (i) A factor VII polypeptide;
   (ii) A buffering agent suitable for keeping pH in the range of from about 4.0 to about 9.0;
   (iii) An agent selected from the list of: a calcium salt, a magnesium salt, or a mixture thereof; wherein the concentration of (iii) is less than 15 mM; and
   (iv) An ionic strength modifying agent; wherein the ionic strength of the composition is at least 200 mM.

2. A composition as defined in claim 1, wherein the ionic strength of the composition is at least 250 mM.

3. A composition as defined in claim 1, wherein the ionic strength modifying agent (iv) is selected from the group consisting of: a neutral salt; an amino acid; a small peptide; and a mixture of at least two of said modifying agents.

4. A composition as defined in claim 3, wherein the ionic strength modifying agent (iv) comprises sodium chloride.

5. A composition as defined in claim 1, wherein the agent (iii) is present in a concentration of at least about 2 mM.

6. A composition as defined in claim 1, wherein the calcium salt is selected from the group consisting of: calcium chloride, calcium acetate, calcium gluconate, and calcium laevulate.

7. A composition as defined in claim 1, wherein the magnesium salt is selected from the group consisting of: magnesium chloride, magnesium acetate, magnesium sulphate, magnesium gluconate, and magnesium laevulate.

8. A composition as defined in claim 1, wherein the agent (iii) is selected from the group consisting of: calcium chloride, calcium acetate, magnesium chloride, magnesium acetate, magnesium sulphate, or a mixture thereof; and wherein the ionic strength modifying agent (iv) is sodium chloride.

9. A composition as defined in claim 1, further comprising a tonicity modifying agent (v).

10. A composition as defined in claim 9, wherein the tonicity modifying agent (v) is selected from the group consisting of: a neutral salt; a mono-, di- or polysaccharide; a sugar alcohol; an amino acid; or a small peptide, or a mixture of at least two of said modifying agents.

11. A composition as defined in claim 9, wherein the tonicity modifying agent (v) is present in a concentration of from about 1 mM to 500 mM.

12. A composition as defined in claim 11, wherein the concentration of the tonicity modifying agent (v) is 10-250 mM.

13. A composition as defined in claim 1, further comprising a non-ionic surfactant (vi).

14. A composition as defined in claim 13, wherein the non-ionic surfactant is a polysorbate or a poloxamer or a polyoxyethylene alkyl ether.

15. A composition as defined in claim 1, further comprising an antioxidant (vii).

16. A composition as defined in claim 15, wherein the antioxidant (vii) is selected from the group consisting of: L- or D-methionine, a methionine analogue, a methionine-containing peptide, a methionine-homologue, ascorbic acid, cysteine, homocysteine, gluthatione, cystine, and cysstathionine.

17. A composition as defined in claim 15, wherein the antioxidant is present in a concentration of from about 0.1 to about 5.0 mg/ml.

18. A composition as defined in claim 1, wherein pH is kept in the range of from about 5.5 to about 6.5.

19. A composition as defined in claim 1, wherein the agent suitable for keeping pH in the range of from about 4.0 to about 7.0 is selected from the group consisting of acids and salts of: MES, PIPES, ACES, BES, TES, HEPES, TRIS, histidine (e.g. L-histidine), imidazole, glycine, glycylglycine, glycinamide, phosphoric acid (e.g. sodium or potassium phosphate), acetic acid (e.g. ammonium, sodium or calcium acetate), lactic acid, glutaric acid, citric acid (e.g. sodium or potassium citrate), tartaric acid, malic acid, maleic acid, and succinic acid, and a mixture of at least two of said agents.

20. A composition as defined in claim 19, wherein the concentration of the agent is from about 1 mM to about 50 mM.

21. A composition as defined in claim 1, which is stable for at least 6 months at 2-80° C.

22. A composition as defined in claim 1, wherein the factor VII polypeptide is selected from the group consisting of human factor VIIa and a factor VII sequence variant.

23. A composition as defined in claim 1, wherein the factor VII polypeptide is present in a concentration of from about 0.1 mg/ml to about 15 mg/ml.

24. A method for preparing a liquid, aqueous composition of a factor VII polypeptide, comprising the step of providing the factor VII polypeptide in a solution comprising a buffering agent (ii) suitable for keeping pH in the range of from about 4.0 to about 9.0; an agent (iii) selected from the group consisting of: a calcium salt, a magnesium salt, and a mixture thereof; wherein the concentration of (iii) is less than 15 mM; and an ionic strength modifying agent(iv); while ensuring that, in the final composition, the ionic strength is at least 200 mM.

25. A method for treating a factor VII-responsive syndrome, the method comprising administering to a subject in need thereof an effective amount of an aqueous liquid composition as defined in claim 1.

26. A method for reducing degradation of a factor VII polypeptide in a liquid formulation, said method comprising the step of providing the factor VII polypeptide in a solution comprising a buffering agent (ii) suitable for keeping pH in the range of from about 4.0 to about 9.0; an agent (iii) selected from the group consisting of: a calcium salt, a magnesium salt, and a mixture thereof wherein the concentration of (iii) is less than 15 mM; and an ionic strength modifying agent(iv); while ensuring that, in the final composition, the ionic strength is at least 200 mM.

27. An air-tight, at least partially filled container containing a liquid, aqueous pharmaceutical composition as defined in claim 1, and optionally an inert gas, said container comprising (i) a wall portion and (ii) one or more closure means not constituting part of said wall portion.

* * * * *